United States Patent [19]

Hench et al.

[11] 4,159,358
[45] Jun. 26, 1979

[54] METHOD OF BONDING A BIOGLASS TO METAL

[75] Inventors: Larry L. Hench; Paul J. Buscemi, both of Gainesville, Fla.

[73] Assignee: Board of Regents, State of Florida, Tallahassee, Fla.

[21] Appl. No.: 798,671

[22] Filed: May 19, 1977

[51] Int. Cl.² .............................................. B05D 3/02
[52] U.S. Cl. ........................................ 427/318; 3/1.9; 3/1.91; 3/1.911; 3/1.912; 3/1.913; 65/59 R; 128/92 C; 128/92 CA; 427/330; 427/398 R; 427/435; 428/432; 428/433; 428/434
[58] Field of Search ................... 427/398 R, 435, 330, 427/318, 374 F, 376 C; 428/432, 433, 434; 65/59 R; 128/92 C, 92 CA; 32/10 A; 3/1.9, 1.91, 1.911, 1.912, 1.913

[56] References Cited

U.S. PATENT DOCUMENTS

| | | | |
|---|---|---|---|
| 2,886,463 | 5/1959 | Liest | 427/330 |
| 3,220,815 | 11/1965 | McMillan et al. | 428/432 |
| 3,370,991 | 2/1968 | Domicone et al. | 65/59 R |
| 3,465,424 | 9/1969 | Deringer | 427/398 R |
| 3,497,376 | 2/1970 | Wieser | 427/435 |
| 3,669,715 | 6/1972 | Meyer | 427/318 |
| 3,922,155 | 11/1975 | Broemer et al. | 3/1.9 |
| 3,981,736 | 9/1976 | Broemer et al. | 3/1.913 |
| 3,987,499 | 10/1976 | Scharbach et al. | 3/1.913 |

FOREIGN PATENT DOCUMENTS 47-20638  7/1968  Japan ................................ 428/432

Primary Examiner—Ronald H. Smith
Assistant Examiner—Sadie L. Childs
Attorney, Agent, or Firm—Dennis P. Clarke

[57] ABSTRACT

A method of bonding a bioglass layer to a metal substrate comprising heating the metal substrate having a roughened, oxidized surface to about a temperature at which the expansion of the metal is substantially equal to that of the bioglass at the temperature above which the thermal expansion of the bioglass is non-linear, immersing the heated metal surface in molten bioglass, the time of immersion being of such duration that the temperature of the metal does not rise substantially above the temperature to which it is heated, allowing the coated substrate to cool whereby the bioglass layer is bonded to the metal substrate by ion diffusion and thermo-mechanical stresses in the bioglass and metal layer are relieved at a substantially equal rate and the product produced by said process.

18 Claims, 3 Drawing Figures

Schematic showing how two different metals can be coated with the same glass. Immersion takes place at working temperature, $T_w$. The glass then cools rapidly to near the softening point, $T_s$. The $T_I$'s for the metals are chosen so that volume expansion for both glass and metal are equal. Slight variations in $T_I$ are made to vary surface stresses.

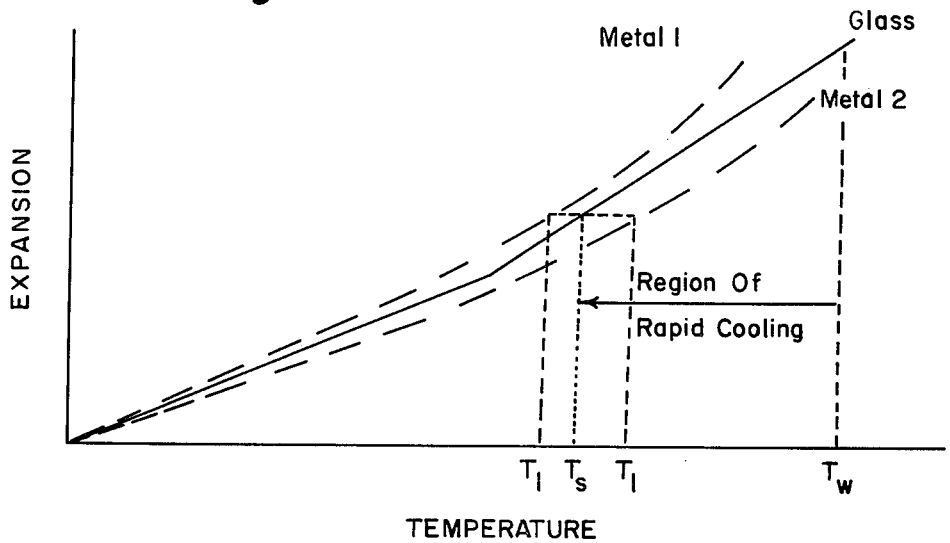

Fig. 1

Schematic showing how two different metals can be coated with the same glass. Immersion takes place at working temperature, $T_w$. The glass then cools rapidly to near the softening point, $T_s$. The $T_1$'s for the metals are chosen so that volume expansion for both glass and metal are equal. Slight variations in $T_1$ are made to vary surface stresses.

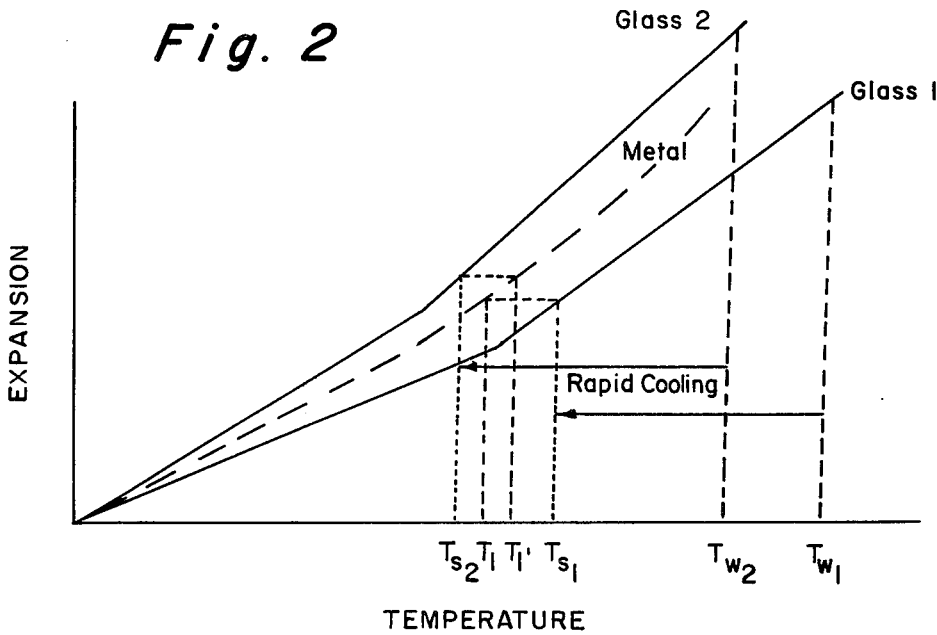

Fig. 2

Schematic showing how a single metal is heated to $T_1$ or $T_1'$ so that volume expansion matches glass 1 or glass 2 respectively. As above, the $T_1$'s are chosen by matching the volume expansion of the glass when it reaches $T_s$.

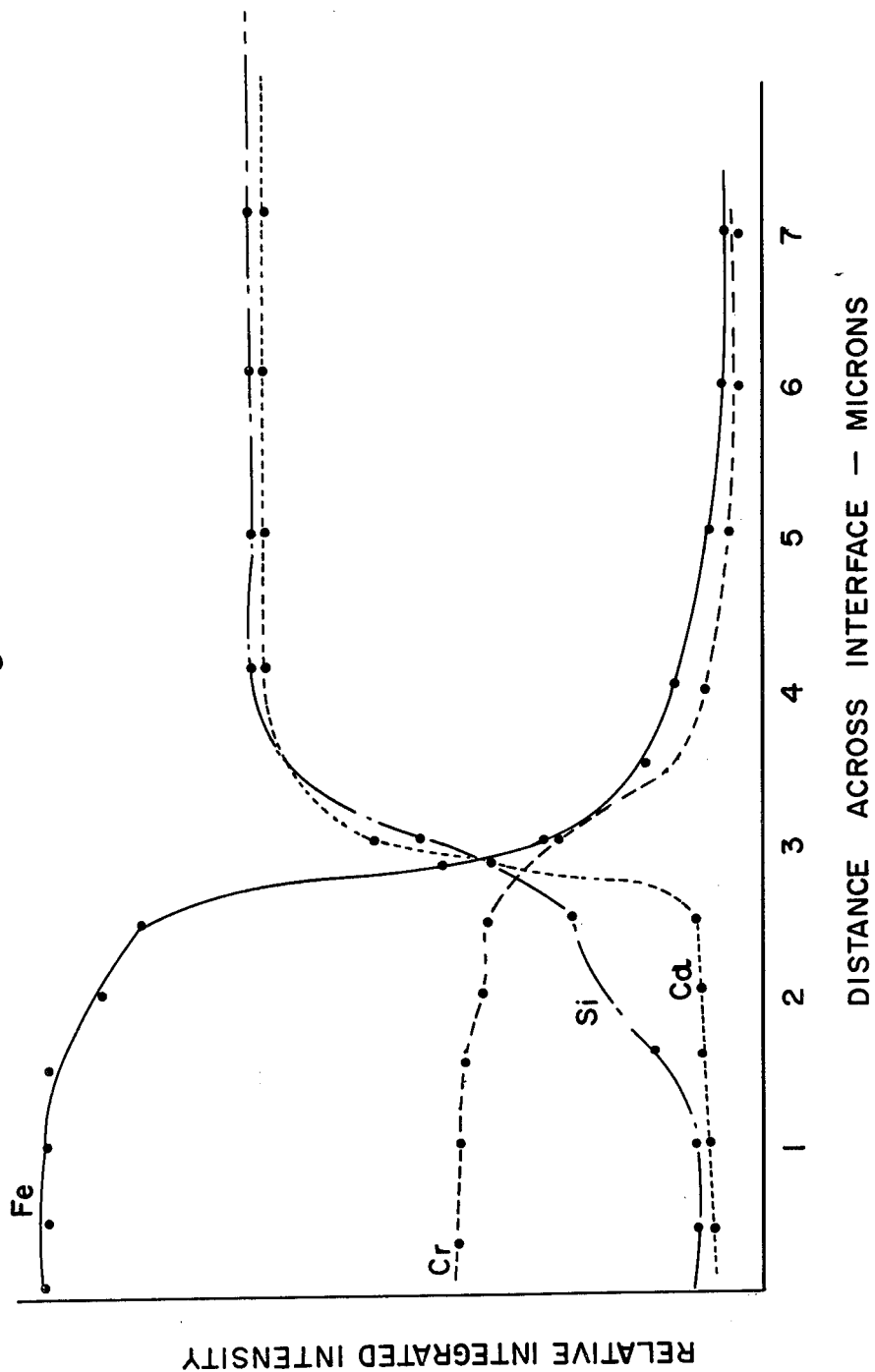

METHOD OF BONDING A BIOGLASS TO METAL

BACKGROUND OF THE INVENTION

It has been proposed to utilize metals for the construction of artificial prostheses and orthopedic and dental devices. The biological inactivity of metal surfaces, however, renders it impossible to achieve cement-free implantation of metal prostheses since bone tissue will not bond or grow thereon.

Various biologically active glasses have recently been introduced for the preparation of artificial prostheses. It is known that bone and other biological tissue will bond to or grow on these biologically active glasses. However, the strength characteristics of the glasses are such that it is impossible to construct sufficiently strong orthopedic or dental devices therefrom.

It has been suggested to overcoat metal substrates with biologically active glasses to provide sufficiently strong orthopedic or dental devices capable of bonding to bone tissue. However, there are numerous difficulties associated with bonding such glasses to metal surfaces. For example, the thermal coefficients of expansion of the metal and glasses are so dissimilar at both the melting and softening points of the glasses that cooling the coated metal substrate results in extreme thermomechanical stresses in the glass and metal layers which, when relieved, cause cracks, etc., in the glass coating.

Prior art methods of coating metals with glasses necessarily require the utilization of glasses and metals which have substantially identical thermal coefficients of expansion and which can withstand those temperatures at which the glass flows. The prior art methods are particularly disadvantageous where it is desired to coat a particular metal with a particular high melting glass in order to obtain a product with specific properties. The problems which normally arise in this connection are:

(1) Excessive scaling of the metal substrate at the elevated temperatures:

(2) Loss of compositional control of the glass through long firing times;

(3) Excessively high diffusion of metal ions into the glass bulk;

(4) The virtual impossibility of matching the thermal coefficients of expansion due to the fact that the choice of glass and metal substrate are fixed because of the desired application of the product.

It is possible to coat metal substrates with mismatched (thermal coefficients of expansion) glass by flame spraying; however, this method gives rise to other disadvantages, namely, high volatilization and loss of glass components, limited choice of glass compositions, extremely high working temperatures and adverse surface reactions on the metal substrate.

It has been proposed to utilize biologically active glasses and metals having similar thermal expansion coefficients; however, this approach drastically limits the number and variety of permissible combinations.

It has also been proposed to coat metal surfaces by applying powder mixtures of the glass thereto and utilizing long firing times and multiple coatings to produce transition layers between the metal and glass having gradient coefficients of expansion to thereby relieve the thermo-mechanical stresses. Obviously, however, this is an expensive and time consuming procedure which, by its very practicality, severely limits the practicality of the ultimate product. German Pat. DT 2,326,100 B2 describes a glass coated material useful as a prosthetic device. However, the German patent requires an intermediate layer of low reactivity glass between the metal substrate and the biologically active glass.

It is an object of the invention to provide an inexpensive method for bonding biologically active glass to metal for the formation of artificial prostheses and orthopedic and dental devices.

SUMMARY OF THE INVENTION

The invention relates to a method of bonding a bioglass layer to a metal substrate comprising:

(1) heating a metal substrate having a roughened, oxidized surface to about a maximum temperature ($T_1$) where said $T_1$ is selected such that the total volume expansion of said metal is substantially equal to that of said bioglass at the temperature ($T_s$) at which the temperature dependence of the volume of said bioglass becomes non-linear, (2) providing a body of molten bioglass at temperature $T_w$ where $T_w$ is sufficiently high that the said bioglass is sufficiently fluid to allow immersion of said metal heated to temperature $T_1$, (3) immersing said metal surface in said molten bioglass for the minimum time required to permit a layer of desired thickness of said bioglass to adhere to said surface upon termination of said immersion, the time of said immersion being of such duration that the temperature of said metal surface does not rise substantially above $T_1$, (4) terminating said immersion, (5) allowing said coating to cool rapidly from $T_w$ to about $T_3$, whereby the thermomechanical stresses in said bioglass layer are rapidly relieved, and (6) allowing said coated substrate to further cool to a temperature below about $T_s$ whereby the thermomechanical stresses in said bioglass coating and said metal surface are relieved at a substantially equal rate due to the substantially linear thermal expansions thereof, said bioglass coating being bonded to said metal surface by ion diffusion through said oxidized surface.

The invention also relates to the product produced by said process.

IN THE DRAWINGS

FIG. 1 represents a graph showing how two metals of differing composition can be coated with the same glass. See Examples 1 and 3. Immersion takes place at the working temperature $T_w$ (temperature of molten bioglass). The glass cools rapidly to near the softening point $T_s$. The $T_1$'s for the metals are chosen so that volume expansion for both glass and metal are substantially equal.

FIG. 2 represents a graph showing how one metal can be coated with bioglass of differing compositions. See Examples 1 and 2. The metal is heated to $T_1$ or $T_1'$ so that volume expansion matches either glass 1 and 2, at $T_{s1}$ and $T_{s2}$, respectively. As in FIG. 1, the $T_1$'s are chosen by matching the volume expansion of the glass when it reaches $T_s$.

FIG. 3 represents a graph showing the degree of diffusion of the elements of the metal and glass across the interface by reason of the coating and diffusion bonding process following the procedure described in Example 1.

DETAILED DESCRIPTION OF THE INVENTION

The present invention is predicated on the discovery that the parameters of the coating operation may be controlled so as to provide a biologically active glass coating on a metal substrate in a simple manner without giving rise to thermo-mechanical stresses, the relief of which results in flaws, etc., in the glass coating.

The application of devices coated according to the invention have been demonstrated with total hip replacement for monkeys, fibula bone section replacement for dogs, stump replacement for goats and bone test sections for rats. Mechanical testing of the metal implants coated according to the invention has shown that the interface between the biologically active glass coating and bone is as strong as that developed between bone and unitary bioglass implants. Moreover, the interface between the metal and biologically active glass is resistant to body fluids and does not fail upon the application of mechanical stresses, even after more than three months in primates. The presence of coatings applied to metals in accord with this invention have shown protection of the coated metal from corrosion even with the metal-glass interface exposed to chloride solutions for more than one year.

As noted above, typical prior art processes utilize multiple coatings of glass on metal substrates to achieve a gradient composition across the interface in order to relive thermo-mechanical stresses.

We have found, however, that at relatively low temperatures, i.e., below about 700° C., the thermal expansion of most metals is virtually linear and that the time required for the expansion of the metal is relatively long (15–30 minutes) as compared to the time required for a surface layer of glass to cool from its molten condition to about 700° C. (less than about 60 seconds). Thus, thermo-mechanical stresses which might develop at an interface between metals and biologically active glasses of different thermal expansion coefficients may be prevented by heating the metal substrate prior to coating only to that temperature ($T_1$) where $T_1$ is chosen such that the total volume expansion of the metal is substantially equal to that of the glass at $T_s$ and where $T_s$ is the temperature at which the thermal expansion of the glass becomes nonlinear. By immersing the heated metal substrate in a molten biologically active glass having a temperature of $T_w$ for a relatively short period of time, i.e., less than about 5 seconds, and immediately withdrawing the substrate from the molten glass, a layer of molten glass is provided on the metal substrate before the metal temperature has had a chance to rise substantially above $T_1$.

The adherent molten glass coating will cool rapidly down to about $T_s$. The flow of the molten glass as it partially solidifies relieves any strains or thermo-mechanical stresses quickly. The composite material then cools more slowly from $T_s$ down to room temperature due to the slow cooling rate of the base metal. This slow cooling allows a gradual contraction of the metal substrate and glass coating at a substantially equal rate due to the linear coefficients expansions at that temperature. These equal rates of contraction allow for relief of the thermo-mechanical stresses and strains without affecting the strength of the bond.

The biologically active glasses, hereinafter termed bioglasses, melt in the range of from about 1250° to about 1550° C. Most metals have a linear thermal coefficient of expansion up to about 700° C. The cooling of the molten glass layer from the elevated melting point temperature down to about 700° C. may be rapid due to the fact that thermo-mechanical stresses therein are relieved as the molten glass flows during solidification.

Any suitable bioglass capable of bonding to bone or other living tissue may be employed in the present invention. Suitable bioglasses include those having the following composition, by weight:

$SiO_2$—40–60%
$Na_2O$—10–32%
$CaO$—10–32%
$P_2O_5$—0–12%
$CaF_2$—0–18%
$B_2O_3$—0–20°

Specific bioglasses include those of the following compositions:

| | Bioglass A | |
|---|---|---|
| $SiO_2$ | | 45.0% |
| $Na_2O$ | | 24.5% |
| $CaO$ | | 24.5% |
| $P_2O_5$ | | 6.0% |
| | Bioglass B | |
| $SiO_2$ | | 42.94% |
| $Na_2O$ | | 23.37% |
| $CaO$ | | 11.69% |
| $P_2O_5$ | | 5.72% |
| $CaF_2$ | | 16.26% |
| | Bioglass C | |
| $SiO_2$ | | 40.0% |
| $Na_2O$ | | 24.5% |
| $CaO$ | | 24.5% |
| $P_2O_5$ | | 6.0% |
| $B_2O_3$ | | 5.0% |

Suitable metals include any metal from which an artificial prosthesis or orthopedic or dental device may be fabricated. Suitable metals include steels such as surgical stainless steel and carbon steel; cobalt-chrome alloys; titanium and titanium alloys; noble metals such as platinum; and noble metal alloys such as platinum (90%) - rhodium (10%) (wt. pcts.) and molybdenum-nickel-cobalt-chrome alloys.

The present invention allows the formation of a bond between the bioglass and the metal without forming intermediate transition or gradient layers therebetween in order to relieve the thermo-mechanical stresses.

It has been found necessary to employ a roughened-oxidized metal surface in order to achieve a sufficiently strong bond between the metal surface and the bioglass layer. Generally, a surface roughness of from about 250 $\mu$m is sufficient. It will be understood, however, that any degree of roughness which substantially increases the surface area of the metal substrate without resulting in a mechanical bond between the metal and the glass is sufficient for the purpose of the invention. If the roughness is not controlled, a mechanical bond may be produced between the glass and the metal, thereby inducing stresses in the glass layer on cooling.

The bioglasses enable the formation of strong bonds between the glass and metals by ion-diffusion. Thus, the glass and metal form a chemical bond by ion-diffusion at the interface. The formation of an oxidized surface enhances the ion-diffusion bonding process.

A relatively thick oxidation surface is created on the metal surface. Generally, oxidation layers of about 0.5 $\mu$m to about 2 $\mu$m in thickness are sufficient. Oxidation of the surface is enhanced by roughening the metal surface. However, the surface roughness of the metal substrate should not be such as to provide mechanical interlocking between the metal and the ultimate glass coating. Uncontrolled rough surfaces will result in residual thermo-mechanical stresses and strains upon cooling.

Any oxidizing atmosphere capable of initiating a chemical reaction involving an electron transfer process between the active oxidizing agent in the atmosphere and the metal may be employed for oxidation. Obviously, the oxidation process will vary depending upon the particular metal and oxidizing atmosphere employed. However, it has been found that subjecting a stainless steel surface to air at about 800° C. for about 20 minutes will result in a sufficiently thick oxidation layer to properly enhance the ion-diffusion bonding of the bioglass to the metal surface.

As noted above, the metal must be heated to that temperature at which the volume expansion of the metal equals that of the glass at the temperature ($T_s$) where the volume expansion of the glass becomes non-linear and subsequently immersed in a molten bioglass for a relatively short period of time, i.e., less than about 5 seconds, in order to provide an adherent coating on the metal surface but insufficient to allow substantial heating of the metal substrate above $T_1$. The time of immersion may be as low as about 2 seconds.

The viscosity of the molten bioglass composition is easily controlled due to its alkali content by merely varying the temperature thereof in increments of 10° C. to 25° C. By varying the viscosity of the molten bioglass, the thickness of the adherent coating on the metal substrate may be effectively controlled. Generally, the process is controlled so as to provide a bioglass coating thickness of about 0.2 mm to about 2 mm on the metal substrate, depending on the particular application of the coated substrate.

Artificial prostheses and orthopedic or dental devices constructed from the bioglass coated metal substrates of the invention are applicable as cement-free implants which are extremely strong and resistant to body fluids.

EXAMPLE 1

A structure designed as a replacement for a total hip joint in a monkey composed of stainless steel having the composition.

| | Wt% | | |
|---|---|---|---|
| C | 0.03 | Impurities (P,S) | <0.3 |
| Mn | 1.5 | Fe | - balance |
| Si | 0.5 | | |
| Cr | 18 | | |
| Ni | 13 | | |
| Mo | 2.25 | | | was thoroughly cleaned by sandblasting with 180 grit alumina at 80 psi to remove foreign scale and roughen the surface to about a 150 μm finish. The roughening increases the surface area of the metal substrate thereby providing more area for a diffusional bond between the glass and metal.

The device is then thoroughly cleaned ultrasonically in acetone three times (at least 10 minute cycle). The device is then suspended in the center of a tubular oxidizing furnace open to the atmosphere and maintained at 800° C. ($T_1$). The device was allowed to remain in the furnace for 20 minutes to allow for complete linear expansion and to provide an oxide finish in the roughened metal surface of about 1-2 μm in thickness.

A biologically active glass having the composition of Bioglass A above was melted in a platinum crucible for a period of 1 hour at 1325° C. The volume of molten glass is sufficient to allow complete immersion of the steel device. The glass is very fluid at this temperature and has a viscosity of about 2 poise.

The metal device and crucible containing the bioglass are simultaneously withdrawn from their respective furnaces. The metal device is immediately immersed in the molten bioglass with a quick, smooth motion and withdrawn at a rate of about 2 cm/sec. This produces a fluid coating of glass of about 1 mm in thickness in the surface of the device. The entire procedure requires about 3–5 seconds. Obviously, variations in the thickness of the bioglass layer may be achieved by controlling the viscosity of the glass, the length of time of residence of the device in the molten glass, and the rate of withdrawal of the device from the glass.

The glass coated device is held in the air for 20 to 30 seconds to allow the surface temperature of the glass to reach about 800° C. During this period the glass flows thereby relieving any induced stresses. Also during this period diffusion of metal from the thin oxide layer into the first few (5) micrometers of glass occurs.

After the temperature of the surface of the glass has cooled to about 700° C., the coated device is placed in a cooling furnace and allowed to cool to room temperature thereby permitting uniform contraction of the glass and metal.

Optionally, the coated device may be re-heated to 500°–700° C. or allowed to remain at 500°–700° C. after coating for a pre-determined period of time to allow for partial or full crystallization of the glass.

EXAMPLE 2

The above procedure is followed employing a similar device composed of the same stainless steel and a bioglass having the composition of Bioglass B above. The temperature of the molten glass is about 1150° C. The resulting coated device was suitable for use as a prosthetic device.

EXAMPLE 3

The above procedure was employed utilizing the bioglass composition of Example 1 and a titanium metal device. The metal device was initially heated to 900° C. in an argon atmosphere with a small partial pressure (<1mm) of oxygen prior to immersion. The atmosphere composition is controlled so as to prevent the oxide layer on the metal from becoming too thick.

Polished surfaces of the interfaces between the metal substrates and glass coatings of Examples 1, 2 and 3 were analyzed by energy dispersive X-rays which revealed that a true chemical or diffusional bond had matured between the glass and metal.

What is claimed is:

1. A method of bonding a bioglass layer to a metal substrate comprising:
    (1) heating a metal substrate having a roughened, oxidized surface to about a maximum temperature ($T_1$) where said $T_1$ is selected such that the total volume expansion of said metal is substantially equal to that of said bioglass at the temperature ($T_s$) at which the temperature dependence of the volume of said bioglass becomes non-linear, (2) providing a body of molten bioglass at temperature $T_w$ where $T_w$ is sufficiently high that the said bioglass is sufficiently fluid to allow immersion of said metal heated to temperature $T_1$, (3) immersing said metal surface in said molten bioglass for the minimum time required to permit a layer of desired thickness of said bioglass to adhere to said surface upon termination of said immersion, the time of said immersion being of such duration that the temperature of said metal surface does not rise substantially above $T_1$, (4) terminating said immersion, (5) allowing said coating to cool rapidly from $T_w$ to about $T_s$, whereby the thermo-mechanical stresses in said bioglass layer are rapidly relieved, and (6) allowing said coated substrate to further cool to a temperature below about $T_s$, whereby the thermo-mechanical stresses in said bioglass coating and said metal surface are relieved at a substantially equal rate due to the substantially linear thermal expansions thereof, said bioglass coating being bonded to said metal surface by ion diffusion through said oxidized surface.

2. The method of claim 1 wherein a predetermined viscosity of the molten bioglass, prior to immersion, is maintained by temperature adjustment in order to control the desired thickness of said adhered layer of bioglass on said metal surface.

3. The method of claim 2 wherein the temperature of said molten bioglass is maintained at between about 1250° C. to about 1550° C.

4. The method of claim 1 wherein said $T_1$ is above about 700° C.

5. The method of claim 1 wherein said metal surface has a degree of roughness below that at which mechanical interlocking between said metal surface and said bioglass coating occurs.

6. The method of claim 1 including the step of oxidizing said roughened metal surface.

7. The method of claim 6 wherein said metal surface is oxidized by exposing said metal surface to an oxidizing temperature at an elevated temperature.

8. The method of claim 1, wherein said metal is a steel, a cobalt-chrome alloy, titanium or titanium alloy, a noble metal or noble metal alloy, or a molybdenum-nickel-cobalt-chrome alloy.

9. The method of claim 8 wherein said steel is stainless steel.

10. The method of claim 8 wherein said steel is carbon steel.

11. The method of claim 1 wherein said bioglass has a moderately high alkali content and is substantially invert with respect to silica content.

12. The method of claim 11 wherein said bioglass contains, by weight:
$SiO_2$—40–62%
$Na_2O$—10–32%
$CaO$—10–32%
$P_2O_5$—0–12%
$CaF_2$—0–18%
$B_2O_3$—0–20%.

13. The method of claim 1 wherein said biologically active glass contains, by weight:
$SiO_2$—45.0%
$Na_2O$—24.5%
$CaO$—24.5%
$P_2O_5$—6.0%.

14. The method of claim 1 wherein said biologically active glass contains, by weight:
$SiO_2$—42.94%
$Na_2O$—23.37%
$CaO$—11.69%
$P_2O_5$—5.72%
$CaF_2$—16.26%.

15. The method of claim 1 wherein said biologically active glass contains, by weight:
$SiO_2$—40.0%
$Na_2O$—24.5%
$CaO$—24.5%
$P_2O_5$—6.0%
$B_2O_3$—5.0%.

16. The method of claim 1 wherein the thickness of said bioglass coating is from about 0.2mm to about 2mm.

17. The method of claim 1 wherein the time of immersion is less than about 5 seconds.

18. The method of claim 6 wherein said metal is a steel and is oxidized by exposure to air at about 800° C. for about 20 minutes.

* * * * *

UNITED STATES PATENT AND TRADEMARK OFFICE
CERTIFICATE OF CORRECTION

PATENT NO. : 4,159,358
DATED : June 26, 1979
INVENTOR(S) : LARRY L. HENCH and PAUL J. BUSCEMI It is certified that error appears in the above-identified patent and that said Letters Patent are hereby corrected as shown below:

Column 7, line 44, "temperature" (first occurrence) should be --atmosphere--.

Signed and Sealed this

Ninth Day of October 1979

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,159,358
DATED : June 26, 1979
INVENTOR(S) : LARRY L. HENCH; and PAUL J. BUSCEMI It is certified that error appears in the above–identified patent and that said Letters Patent are hereby corrected as shown below:

Please add the following paragraph at the end of the specification and before claims:

--This invention was made with Government support under Contract Number DADA17-70-C-0001 awarded by the Department of the Army. The Government has certain rights in this invention.--

Signed and Sealed this

Twenty-first Day of September 1982

[SEAL]

Attest:

Attesting Officer

GERALD J. MOSSINGHOFF

Commissioner of Patents and Trademarks